United States Patent [19]
Martinez

[11] Patent Number: 4,637,412
[45] Date of Patent: Jan. 20, 1987

[54] DEVICE FOR STORING DENTAL FLOSS AND FOR FORMING THREE SEPARATELY-USABLE STRIPS OF FLOSS FOR USE WITH TENSIONING MEANS

[76] Inventor: Armando Martinez, 4749 Hackett Ave., Lakewood, Calif. 90713

[21] Appl. No.: 749,517

[22] Filed: Jun. 27, 1985

[51] Int. Cl.$^4$ ............................................. A61C 15/00
[52] U.S. Cl. .................................... 132/92 R; 132/91; 403/26; 403/383
[58] Field of Search ..................... 132/92 A, 92 R, 89, 132/90, 91, 93; 403/26, 354, 383

[56] References Cited

U.S. PATENT DOCUMENTS

| | | | |
|---|---|---|---|
| 918,281 | 4/1909 | Chambers | 132/91 |
| 1,091,789 | 3/1914 | Andren | 132/91 |
| 1,640,607 | 8/1927 | Kitley | 132/92 A |
| 1,644,390 | 10/1927 | Miller | 132/91 |
| 1,833,671 | 11/1931 | Byars | 132/92 R |
| 1,970,575 | 8/1934 | Reitzel | 132/91 |
| 2,093,321 | 9/1937 | Kempton | 403/383 |
| 2,117,844 | 5/1938 | Grieco | 132/92 R |
| 2,187,442 | 1/1940 | Beach | 132/92 R |
| 2,644,469 | 7/1953 | Cohen | 132/92 R |
| 3,592,203 | 7/1971 | Johnson | 132/91 |
| 3,693,638 | 9/1972 | Ciccarelli | 132/91 |
| 3,746,017 | 7/1973 | Casselman | 132/92 A |
| 3,993,085 | 11/1975 | Skinner | 132/92 A |
| 4,008,728 | 2/1977 | Sanchez | 132/92 R |
| 4,151,851 | 5/1979 | Bragg | 132/91 |

FOREIGN PATENT DOCUMENTS 2141935  1/1985  United Kingdom ................ D28/64

*Primary Examiner*—John J. Wilson
*Attorney, Agent, or Firm*—Milton S. Gerstein

[57] ABSTRACT

A device for storing dental floss and paying the floss out is disclosed, which device provides three separately-usable strips of dental floss for use to floss teeth. The three strips form a U-shaped loop, and are tightened, or tensioned, for use by a tensioning means made up of an axle with a slot formed at each end, through which portions of the first and third strips of floss pass, which first and third strips are parallel to each other. The axle is mounted for conjoint rotation with a ratchet wheel which is allowed rotation in only one direction by an associated pawl. A thumb wheel mounted for rotation with the ratchet wheel and axle is rotatable by the user of the device to continually tension the strips of floss for use, which rotation of the thumb wheel is easily done by one hand of the user. The axle is readily removable from the thumb wheel and ratchet wheel, and is rotatable with them by a non-circular part formed in the central portion thereof, which non-circular part mates with the non-circular openings in each of the thumb wheel and ratchet wheel.

5 Claims, 7 Drawing Figures

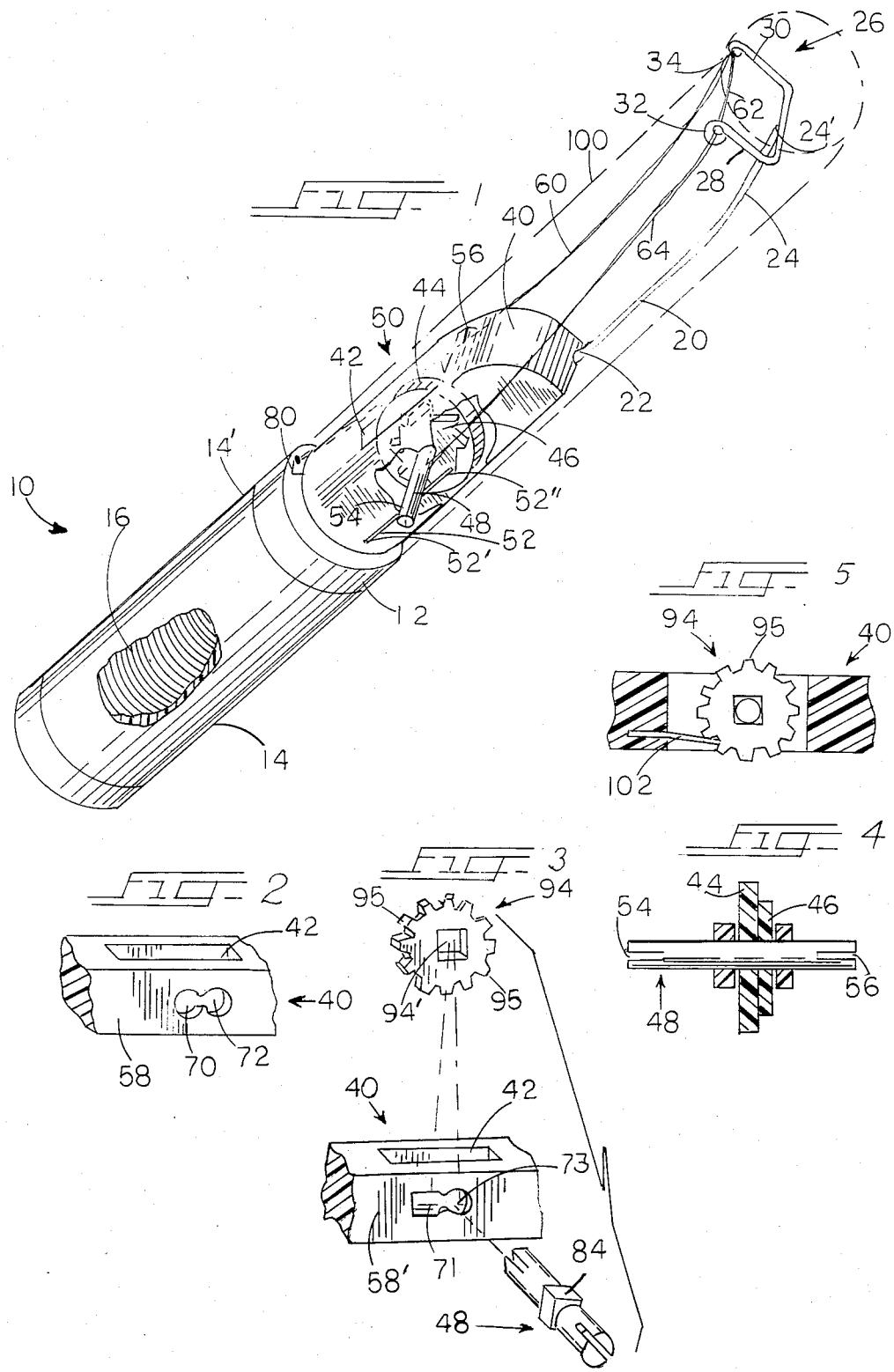

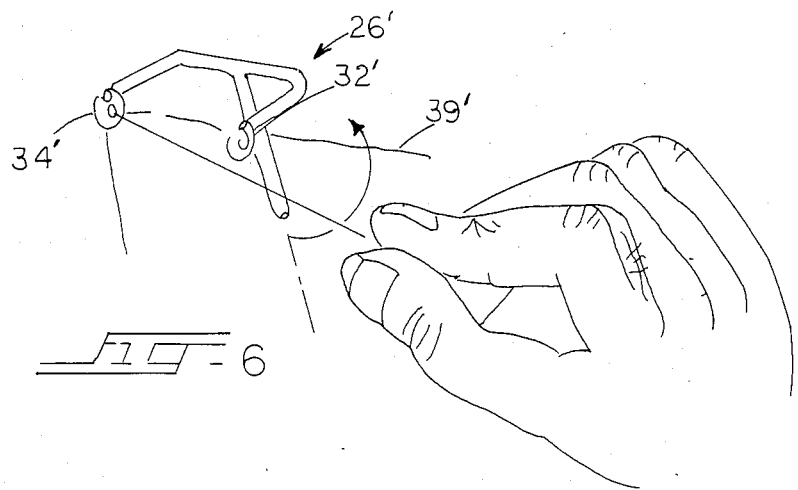
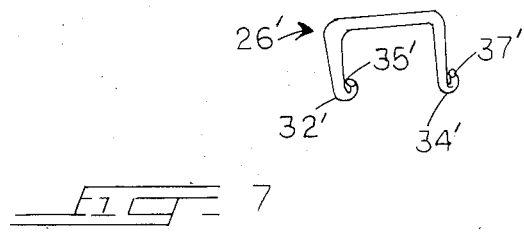

DEVICE FOR STORING DENTAL FLOSS AND FOR FORMING THREE SEPARATELY-USABLE STRIPS OF FLOSS FOR USE WITH TENSIONING MEANS

BACKGROUND OF THE INVENTION

The present invention is directed to a device for firstly storing a supply of dental floss, and thereafter paying it out to form three separately-usable strips of floss, each strip being used for flossing by itself. Dental floss supply and strip-provision means are known, an example of one being disclosed in U.S. Pat. No. 4,151,851, to Bragg. Other devices are known, but all suffer from the disadvantage that proper tensioning of the floss to be used is difficult to achieve in combination with the paying out of the floss from the supply. Such tensioning of the floss for use has hitherto been achieved only by the use of two hands of the user, making it time-consuming, difficult, and, at times, frustrating. Further, prior art devices have only provided one, relatively short length of floss for use, that is quickly used up, with the necessity of advancing the floss to bring a new, fresh portion to the area where it may used.

SUMMARY OF THE INVENTION

It is, therefore, the primary objective of the present invention to provide a dental flossing device that not only supplies the dental floss to be used, but supplies three separately-usable strips of floss for use, each being capable of use for desired spaces between the teeth. It is another objective of the present invention to provide a dental flossing device which has a tensioning mechanism that allows for quick, easy, and sure tightening of the floss for use. It is still another objective of the present invention to provide a dental flossing, device that may easily allow for such tensioning of the usable floss by just one hand of the user of the device.

It is another objective of the present invention to allow for easy and simple disassembly of the parts of the device for cleaning and replacement.

Toward these and other ends, the flossing device of the present invention is provided with a main body which has a hollow interior portion for storing a supply of dental floss. The housing has an exterior, circumferential slot through which the floss from the supply may pass to a tensionsing mechanism, and thence to a guide means for forming the three separately-usable strips of floss. The tensioning mechanism includes an axle with a slot formed at each end thereof through which the length of floss passes. The floss first passes through one of the slots of the axle, and then to the guide means, and then to the other slot of the axle.

The guide means includes an elongated, stiff wire element having a distal end provided with a bracket forming a pair of eyelets, through which the length of floss is inserted before connection with the other of the pair of slots of the axle. The eyelets are raised above the plane in which the first end of the wire element in contained, so that each of the strips forming the U-shaped loop of usable dental floss may be used to floss the teeth. To tension the usable floss, a ratchet wheel is provided which is limited to rotation in one direction only by a pawl. A thumb wheel operatively connected with the axle and ratchet wheel for conjoint rotation is also provided for allowing easy rotation of the axle by the thumb of the user. By rotating the thumb wheel, the axle is rotated, to thus tension the length of floss extending between the two slotted ends of the axle for the U-shaped loop thereof, and the eyelets of the guide means. Since rotation of the axle is prevented in the other direction, release of the thumb wheel does not cause the loosening of the tension of the length of usable floss.

BRIEF DESCRIPTION OF THE DRAWING

The invention will be more readily understood with reference to the accompanying drawing, wherein FIG. 1 is a perspective view showing the novel dental flossing device of the present invention;

FIG. 2 is a perspective view showing the housing of the device of FIG. 1 which houses the thumb wheel and ratchet wheel of the invention;

FIG. 3 is an assembly view of a modification of the novel dental flossing device of the present invention showing the arrangement of the tensioning shaft and thumb wheel, which thumb wheel serves in this modification as a ratchet wheel also;

FIG. 4 is a cross-sectional view showing the modification of the novel dental flossing device of the present invention shown in FIG. 3, in which the thumb wheel serves also as the ratchet wheel; and FIG. 5 is a cross-sectional view showing the preferred embodiment of FIG. 1, where there are provided both the thumb wheel and separate ratchet wheel.

FIGS. 6 and 7 show perspective views showing a modification of the eyelets.

DETAILED DESCRIPTION OF THE INVENTION

Referring now to the drawing in greater detail, in FIG. 1 there is shown the novel dental floss dispensing device of the present invention, which is indicated generally by reference numeral 10. The dental floss device 10 includes a main body portion 12 of substantially cylindrical shape, which portion 12 threadingly mounts a handle portion 14 having a substantial hollow interior for storing therein a supply of dental floss, such as spool 16. The handle portion 14 is suitably threaded at its forward end 14' for mating engagement with the threaded end of the main body portion 12, so that the handle portion 14 may be selectively removed to insert a fresh supply of dental floss and to remove the old spool. The handle portion 14 has a suitable circumferential opening formed therein adjacent the forward end 14' through which the lead end of dental floss from the spool 16 is guided for subsequent passage to the guide means of the present invention.

The guide means of the present invention includes an elongated wire element 20 having a first end 22 fixedly attached to a forward portion of the tensioning mechanism of the present invention, to be described below in greater detail. The elongated wire element 20 has a forward portion 24 that extends at an angle with respect to the rest of the element 20, as clearly shown in FIG. 1. This angled or upwardly bent portion 24 has a forward-most end 24' that lies in a horizontal plane substantially elevated with respect to the end 22. Formed integrally with the end 24' is a bracket member 26 having a first upwardly extending leg 28 and a second upwardly extending leg 30. Each leg is formed with an eyelet 33 and 34, respectively, at the uppermost portion thereof, which eyelets thread therein portions of the floss from the supply spool 16, in the manner to be described. The eyelets 32 and 34 lie in a horizontal plane approximately coplanar with the upper surface of the main body portion 12 and the upper surface of the housing 40 for the tensioning device to be described, so that as the floss is guided through the tensioning device and threaded through the eyelets 32 and 34, the lengths or strips of dental floss thus formed extend angularly upwardly from the main body portion 13 to the eyelets 32 and 34, to thus ensure that each strip of floss is usable to clean between spaces of the teeth. The tensioning device 50 of the present invention is used to make the lengths or strips of floss taut for use to clean the spaces between teeth. The tensioning device 50 includes main housing 40 having a substantially rectangular-shaped hollow central cut-out portion 42 in which is rotatably mounted a thumb wheel 44, a ratchet wheel 46, and axle 48. The ratchet wheel 46 is connected to the thumb wheel 44 for conjoint rotation, so that as the thumb wheel is rotated in the counter-clockwise direction, when viewing FIG. 1, the ratchet wheel 46 is rotated therewith. The ratchet wheel, and therefore the thumb wheel 44, is prevented from rotating in the clockwise direction, when viewing FIG. 1, by a pawl-type element 52, which in the embodiment shown in FIG. 1 takes the form of an elongated steel spring affixed at its first end 52' to the forward surface of the main body surface 12. The second spaced end 52" of the spring strip is contained in a lower plane through which the teeth of the ratchet wheel pass, the end 52" serving to prevent rotation of the ratchet wheel in the clockwise direction in the well-known manner. The diametric extension of the thumb wheel 44 is larger than the depth of the hollow inner cut-out 42 of the housing, so that the upper portion of the thumb wheel projects above the top surface of the housing 40 to allow easy and ready access to the thumb of the user of the device for rotating the thumb wheel in the counter-clockwise direction.

The axle 48 is provided with a groove or slot at each end 54 and 56 of the axle, as shown in FIG. 1. These slots are used for threading the floss therethrough, such that when the lead end of the floss is removed from the handle portion and pulled toward the eyelets, the floss is first threaded through the slot in the end 56 of the axle, and from there threaded through eyelet 34, and thence to eyelet 32, and from there, the floss-end is threaded in the slot of the end 54 of the axle. Upon such threading of the floss, the thumb wheel is rotated in the counter-clockwise direction, when viewing FIG. 1, until the the floss is wrapped about the ends 54 and 56 of the axle in sufficient amounts so as to tension the strips of the floss extending between the axle ends and the guide eyelets 32 and 34. Upon release of the thumb wheel, reverse rotation of the axle is prevented by the pawl and ratchet mechanism, to ensure that the floss stays taut and in condition for use for cleaning the spaces between teeth. While the axle is rotated to make the floss taut and tensioned, each of the three strips 60,62, and 64 of the floss is tensioned simultaneously, with each strip being capable of ready use for cleaning the spaces between the teeth. If, during flossing, one or more of the strips 60, 62, and 64 should become loose , the user simply rotates the thumb wheel again in the counter-clockwise direction by his thumb, to again place the strips in tension. After use, the strip of floss is simply cut off by knife blade 80 mounted to the forward surface of the main body portion 12. After such cutting, a new length of floss may then threaded in the same manner through end 56 of the axle, through eyelets 34 and 32, and then end 54 of the axle, whereupon the axle is again rotated to wind the floss about the ends of the axle to make the strips taut for use.

FIG. 2 shows the housing 40 in greater detail. The housing 40 is a block-shaped element for most of its length and has a pair of side walls through which are formed a pair of joined or connected holes. In the side wall 58 shown in FIG. 2, the pair of joined or connected holes 70 snd 72 form a figure "8" appearance. The hole 70 is used for assembling and disassembling the axle 48 and thumb wheel 44 and ratchet wheel 46, for replacement of parts, and for cleaning thereof. The other side wall 58' is also provided with a pair of holes 71 and 73. However, the hole 71 is quadrilateral in shape, with the hole 73 being circular, as holes 70 and 72. The hole 71 is also used for assembling and disassembling the parts, and allows for passage of the quadrilateral-shaped central part 84 of the axle 48, which mates with the similar-shaped ,quadrilateral central openings of the thumb wheel 44 and ratchet wheel 46. In FIG. 3, only the thumb wheel 44 is shown, which thumb wheel 94 serves both as thumb wheel 44 and as ratchet wheel 46, in a modification of the tensioning device of FIG. 1. However, it is to be understood that the embodiment of FIG. 1 is structured along similar lines, in that the axle has a quadrilateral-shaped central connection for mating engagement with the quadrilateral central openings of the both the thumb wheel 44 and ratchet wheel 46. The central opening 94' of wheel 94 receives therein the central quadrilateral connecting piece 84 for driving connection. The opening 71 allows for insertion of the connecting piece 84 therethrough, after which the axle 48 is slid to the right, when viewing FIG. 3, to thus keep in place the entire assembly. To remove the parts, the procedure is reversed.

In the embodiment of the tensioning device shown in Figs. 3–5, as previously described, the thumb wheel 94 serves also as the ratchet wheel. Toward this end, the wheel 94 is provided with a series of teeth-like serrations 95 which define spaces 95' therebetween. As shown in FIG. 5, the pawl-like element in this embodiment is also a steel spring, elongated strip 102 having a first end fixedly connected in the rearward portion of the housing 40, and a second end that is received in a space 95' for preventing rotation of the wheel 94 in one direction while allowing rotation in the other direction. The element 102 is bent toward its second end, as shown in FIG. 5, so that rotation of the wheel 94 is permitted in the counter-clockwise direction, when viewing FIG. 5, but is prevented rotation in the clockwise direction. The bent portion bends downwardly, as viewed in FIG. 5 to prevent such clockwise rotation.

A transparent covering tube 100 is also provided for protecting the parts of the device when not in use. Such cover typically snaps on to the main body portion in a conventional manner.

Though specific embodiments of the invention have been shown and described, it is to be understood that numerous changes and modifications may be made therein without departing from the scope and spirit of the invention as set out in the appended claims.

As can be seen in FIGS. 6 and 7, a modification of the eyelets are indicated by reference numerals 32' and 34' for the bracket member 26'. Each eyelet 32' and 34' allows for easy and fast threading of the floss by means of a spiral wire element making up the eyelet. Each spiral element provides a miniature opening indicated by reference numerals 35' and 37' through which the dental floss may be inserted for threading, in the manner shown in FIG. 6 by a hand. First, the floss is threaded through the eyelet 34' through its opening 37', and secondly inserted through the opening 35' in the eyelet 32'. Dot-dash line 39' in FIG. 6 indicates the final state of the floss after having been threaded through the two eyelets. The threading of each eyelet via respective openings 35' and 37' is achieved in a simple manner by merely rotating the floss portion in the vicinity of the eyelet to be threaded in the counterclockwise direction when viewing FIG. 6. Owing to the subsequent tension placed on the floss by the tensioning means, there is little or no possibility of the floss escaping from the eyelets since each opening 35' and 37' faces away from the direction that the floss portions therein are pulled during tensioning. That is, the openings 35' and 37' face upwardly.

What I claim is:

1. A dental flossing device for storing a spool of floss and allowing the use thereof in a ready and continually adjustable manner, comprising:

a main body portion having a hollow interior thereof for storing a spool of dental floss for paying out the dental floss;

elongated floss guide means having a first end toward said main body portion, and a second end remote therefrom and projecting away from said main body portion so as to define a length by which the dental floss may be extended, said second end of said guide means comprising a first threading and retaining means for a portion of the dental floss, and a second threading and retaining means for another portion of the dental floss, whereby dental floss from the spool may be extended from said main body portion along said guide means and through said first and second threading and retaining means;

means for continually tensioning the dental floss, said means for tensioning comprising a rotatably mounted wheel means, housing means for said wheels means for mounting said wheel means to said main body portion, and a shaft mounted for rotation with said wheel means, said shaft passing through the center of said wheel means such that said wheel means is rotatable in a plane perpendicular to the length of said shaft; said shaft having a first end projecting outwardly of a side surface of said housing having a first groove formed therein, and a second end projecting from another side surface of said housing having a second groove formed therein;

means for conjointly connecting said wheel means and said shaft so that when said wheel means is rotated, said shaft is rotated in unison therewith;

means formed in said side surfaces of said housing for allowing disassembly of said wheel means and said shaft from said housing for cleaning and replacement of parts and for rotatably mounting said first and second ends of said shaft;

means for limiting the rotation of said wheel means and said shaft to only one direction and preventing the rotation thereof in the other direction; and said housing having a receptacle thereof for mounting therein said wheel means, said wheel means having a circumferential portion of said wheel means projecting beyond said housing to allow access thereto of a finger for rotating said wheel means; wherein the detal floss from the spool may be inserted through said first groove before threading in said first and second threading and retaining means, and inserted through said second groove after threading in said first and second threading and retaining means, said plane of rotation of said wheel means being parallel to the direction from said first end of said guide means toward said second end of said guide means.

2. The device according to claim 1, wherein said means formed in said side surfaces of said housing comprises at least one opening in one of said side surfaces, and a pair of overlapping openings in the other of said side surfaces, one of said pair defining a substantially approximate polygonal shape.

3. The device according to claim 2, wherein said means for conjointly connecting said shaft to said wheel means for conjoint rotation comprises a polygonal-shaped member between said first and second ends of said shaft having a diametric extension greater than the diameter of said shaft; said wheel means having a similarly-shaped polygonal central opening for mating engagement with said polygonal-shaped member.

4. The device according to claim 3, wherein the other of said pair of openings is circular in shape and has a diameter less than the diametric expanse of said polygonal-shaped member; said polygonal-shaped opening having a diametric expanse greater than the diamtetric expanse of said polygonal-shaped member to allow passage thereof through said polygonal-shaped opening, while preventing the removal thereof when a respective said shaft end is moved into said other of said pair of holes.

5. In a mounting arrangement for mounting a wheel, and the like, via shaft in a housing so as to allow for conjoint rotation of the shaft and wheel and easy disassembly thereof from the housing and from each other, the improvement comprising:

said wheel having a central opening of noncircular shape through which extends said shaft;

said shaft having an enlarged center portion of the same shape as said central opening of said wheel;

said housing having a first side face and a second parallel side face, said first side face having a circular opening therethrough for the projection of one end of said shaft, and said second face having a pair of overlapping openings, one of said pair being substantially circular in shape, and the other of said pair noncircular.

* * * * *